US007686018B2

(12) United States Patent
Cerbini

(10) Patent No.: US 7,686,018 B2
(45) Date of Patent: Mar. 30, 2010

(54) FACE MASK FOR THE PROTECTION AGAINST BIOLOGICAL AGENTS

(76) Inventor: Stefano Cerbini, Via Torricelli 10, Pesaro (IT) I-61100

( * ) Notice: Subject to any disclaimer, the term of this patent is extended or adjusted under 35 U.S.C. 154(b) by 496 days.

(21) Appl. No.: 10/589,874

(22) PCT Filed: Feb. 10, 2005

(86) PCT No.: PCT/IT2005/000060

§ 371 (c)(1),
(2), (4) Date: Aug. 18, 2006

(87) PCT Pub. No.: WO2005/077214

PCT Pub. Date: Aug. 25, 2005

(65) Prior Publication Data

US 2007/0157932 A1 Jul. 12, 2007

(30) Foreign Application Priority Data

Feb. 18, 2004 (IT) .......................... PS2004A0007

(51) Int. Cl.
*A61M 11/00* (2006.01)

(52) U.S. Cl. ................................................ 128/205.29

(58) Field of Classification Search ............ 128/206.21, 128/205.29

See application file for complete search history.

(56) References Cited

U.S. PATENT DOCUMENTS

| | | | | |
|---|---|---|---|---|
| 3,521,630 | A | 7/1970 | Westbberg et al. | |
| 4,130,487 | A * | 12/1978 | Hunter et al. | 210/85 |
| 4,141,703 | A * | 2/1979 | Mulchi | 96/132 |
| 4,239,716 | A * | 12/1980 | Ishida et al. | 264/86 |
| 4,536,440 | A | 8/1985 | Berg | |
| 4,883,052 | A | 11/1989 | Weiss et al. | |
| 5,143,061 | A * | 9/1992 | Kaimer | 128/206.24 |
| D347,299 | S * | 5/1994 | Bryant et al. | D16/313 |
| 5,403,304 | A * | 4/1995 | Ishida | 604/403 |
| 5,509,436 | A | 4/1996 | Japuntich et al. | |
| 5,910,567 | A * | 6/1999 | Tanaka et al. | 528/491 |
| 6,125,849 | A * | 10/2000 | Williams et al. | 128/206.12 |
| 6,354,296 | B1 * | 3/2002 | Baumann et al. | 128/206.19 |
| 6,584,976 | B2 * | 7/2003 | Japuntich et al. | 128/206.15 |
| 7,188,622 | B2 * | 3/2007 | Martin et al. | 128/206.15 |
| 7,371,464 | B2 * | 5/2008 | Sherman et al. | 428/447 |

* cited by examiner

*Primary Examiner*—Steven O Douglas
(74) *Attorney, Agent, or Firm*—Young & Thompson

(57) ABSTRACT

The invention relates to a new mask for the protection against biological agents having additional features to improve the efficiency. The mask is in particular equipped with a filtering layer providing outstanding performances against biological agents, with a high efficiency exhalation valve and with a boundary sealing layer to enhance the seal between mask and face.

10 Claims, 5 Drawing Sheets

13a

13b

13c

13d

13e

FACE MASK FOR THE PROTECTION AGAINST BIOLOGICAL AGENTS

FIELD OF THE INVENTION

The present invention concerns a mask having high filtering properties against biological agents and additional features to improve the efficiency.

BACKGROUND ART

Protective masks are used in a wide variety of applications to protect the human's respiratory system from particles suspended in the air, from powders as well as from solid and liquid aerosols.

The masks generally fall into two categories, molded cup-shaped masks and fold-flat masks.

Molded cup-shaped masks are described, for example, in GB-A-1 569 812, GB-A-2 280 620, U.S. Pat. No. 4,536,440, U.S. Pat. No. 4,807,619, U.S. Pat. No. 4,850,347, U.S. Pat. No. 5,307,796, U.S. Pat. No. 5,374,458.

Fold-flat masks, which can be kept flat until needed, are described, for example, in WO 96/28217, in U.S. patent application Ser. No. 08/612,527, in U.S. Pat. No. 5,322,061, U.S. Pat. No. 5,020,533, U.S. Pat. No. 4,920,960 and U.S. Pat. No. 4,600,002.

The masks are formed from one or more layers of air-permeable materials, typically from an inner layer, a filtering layer and a cover layer.

The filtering layer is normally made from a non woven fabric, in particular from melt-blown microfibers, as disclosed, for example, in U.S. Pat. No. 5,706,804, U.S. Pat. No. 5,472,481, U.S. Pat. No. 5,411,576 and U.S. Pat. No. 4,419,993. The filter material is typically polypropylene.

The filtering material may also contain additives to enhance filtration performances such as, for example, the additives described in U.S. Pat. No. 5,025,052 and U.S. Pat. No. 5,099,026.

The material may also incorporate moisture and mist resistant agents (U.S. Pat. No. 4,874,399, U.S. Pat. No. 5,472,481, U.S. Pat. No. 5,411,576) or electric charge can be imparted to the material (U.S. Pat. No. 5,496,507, U.S. Pat. No. 4,592,815, U.S. Pat. No. 4,215,682).

The outer coverweb protects the filtering layer from abrasive forces. The coverweb is normally made from non woven fibrous materials, typically from polyolefins, polyesters or polyamides. Examples are described in U.S. Pat. No. 4,807,619 and U.S. Pat. No. 4,536,440.

The inner layer has shape-retaining function and is normally made from non woven fabric, typically from polyester.

When the air passes through the mask, the filtering layer removes the contaminants from the flow stream preventing the wearer from inhaling them. Analogously the exhaled air, passing through the mask, is purged from pathogenous agents and from contaminants preventing other persons from being exposed.

Some masks are equipped with an exhalation valve which opens, when the wearer exhales, in response to increased pressure, while closes, during inhaling, forcing the air to pass through the filtering medium.

Examples of masks equipped with valves can be found in U.S. Pat. No. 4,827,924, U.S. Pat. No. 347,298, U.S. Pat. No. 347,299, U.S. Pat. No. 5,509,436, U.S. Pat. No. 5,325,892, U.S. Pat. No. 4,537,189, U.S. Pat. No. 4,934,362, U.S. Pat. No. 5,505,197, US 2002023651.

In order to improve the seal between the mask and the face, the masks may also include additional features such as nose clips, as described in U.S. Pat. No. 5,558,089, and bands, as described in U.S. Pat. No. 4,802,473, U.S. Pat. No. 4,941,470 and U.S. Pat. No. 6,332,465.

Despite the several kinds of available masks, continues efforts are being made in finding new protective means having improved properties in comparison with the existing art.

SUMMARY OF THE INVENTION

The invention provides a mask having high filtering properties against biological agents and additional features to improve the efficiency. The mask is in particular equipped with a filtering layer providing outstanding performances against biological agents, with a high efficiency exhalation valve and with a boundary sealing layer to enhance the seal between mask and face.

DESCRIPTION OF THE PREFERRED EMBODIMENTS

The present invention provides a mask useful as protection against biological agents.

The mask can be fold-flat or cup-shaped. The fold-flat kind is preferred and the following description concerns that.

Figure 1:
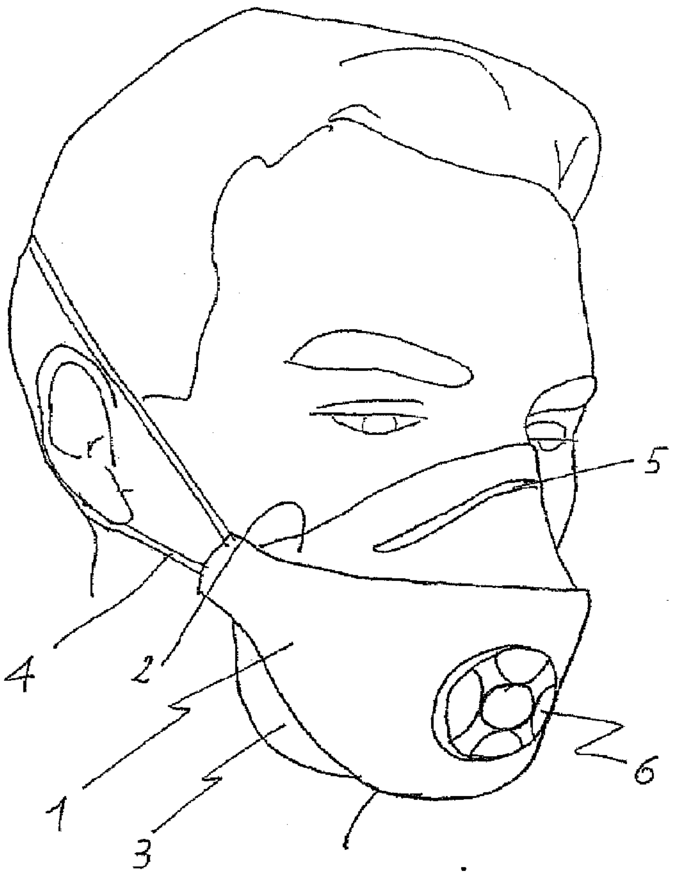
FIG. 1 shows the structure of the mask.

The structure of the mask will be described with reference to FIG. 1, which shows the mask in an opened condition on the face of a wearer, and to FIG. 2, which shows the inside of the mask.

The mask body provides a cup-shaped chamber over the nose and the mouse of the wearer and comprises a central panel 1, an upper panel 2 and a lower panel 3, joined together by conventional means, such as, mechanical clamping, seam, adhesive bonding or heat welding.

Elastic bands 4 secure the mask to the head of the person while a nose clip 5 is provided inside the upper panel 2 to enable the mask to be fitted closely to wearer's face over the nose and cheeks.

A valve 6 is optionally located on the outside of the central panel 1 to facilitate the passage of exhaled air from the mask interior to the ambient air.

The mask can be folded flat for storage by turning the upper and the lower panels 2 and 3 down behind the central panel 1.

The panels 1, 2 and 3 have the same composition and comprise a plurality of layers, at least one of them having filtering functions, being composed of borosilicate micro-glass fibers bound together by a vinyl acetate resin. In this layer the fiber matrix is supported by a strong, cellulose based, substrate which provides strong handling capabilities. The structure is treated with a silicone based coating to impart hydrophobic properties.

By way of example, the multilayer panel can be made from 3 layers a central layer having filtering function an inner layer having shape-retaining function, and an outer layer having covering function.

The dimensions and the weight of the material as well as of the single layers can vary within broad ranges, considering that the materials consist in fiber structures. Some typical values are indicated in the present description but they do not imply any limitation.

In the case of a three layer composition, the material as a whole, can have a thickness typically comprised between 500 and 1000 microns and unit area typically ranging between 130 and 250 g/m$^2$.

The inner layer provides support for the filtration layer and structure to the mask body. The inner layer is made from non-woven fabric obtained, for example, by polypropylene or polyester fibers, typically by polypropylene fibers. The inner layer's thickness typically ranges between 100 and 180 microns and its unit area ranges between 25 and 45 g/m$^2$.

The outer layer protects the filtration layer from abrasion. The outer layer is made from non-woven fabric obtained by polyolefins, polyester or nylon fibers, typically by meltblown polypropylene fibers.

The thickness typically ranges between 250 and 420 microns and the unit area is comprised between 80 and 140 g/m$^2$.

The central layer provides filtration properties and is composed of borosilicate micro-glass fibers bound together by a vinyl acetate resin, the fiber matrix being supported by a cellulose based substrate and the structure being treated with a silicone based coating.

Typically, the central layer has thickness ranging between 150 and 400 microns and unit area ranging between 25 and 65 g/m$^2$.

The composition of the central layer ensures high filtering properties against biological agents, in particular against common bacteria and viruses as well as against dangerous microorganisms such as, for example, anthracis and tubercolosis virus, HBV and HCV.

The efficacy of the filtering material has been proved by several tests. Two of the tests are hereunder described.

Test 1

Monodispersed Challenge of *Mycobacterium Tubercolosis*

The test was carried out to check the efficiency of the filtering material, using a *Mycobacterium tubercolosis* stock (H37Rv).

The method is called "aerosol monodispersed bacteria challenge" and is considered very significant as the diffusion of tubercolosis within sanitary environments takes mainly place in the form of aerosol droplets coming from infected people.

Figure 3:
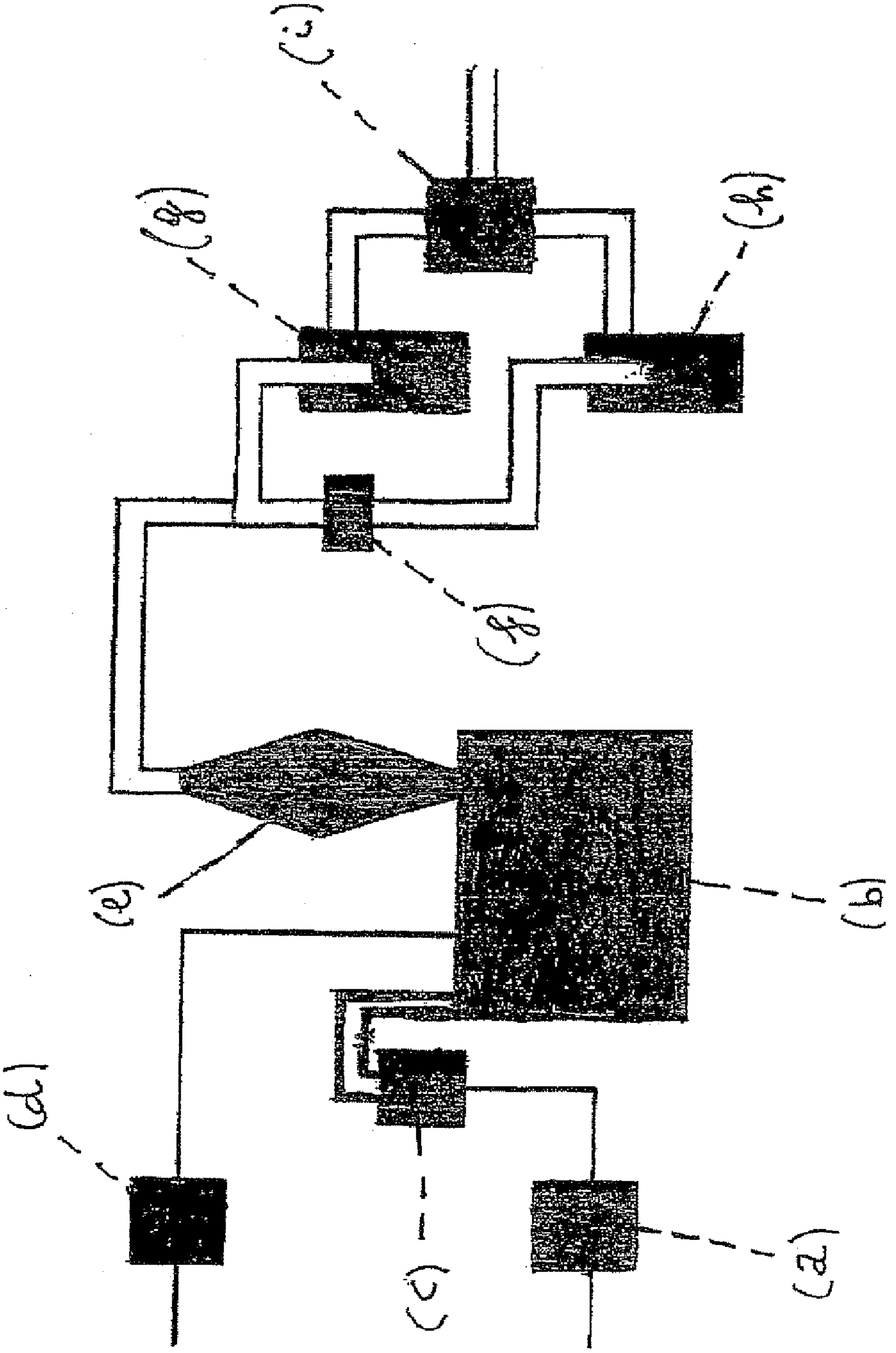
FIG. 3 concerns a test run using the apparatus schematically shown.
Figure 4:
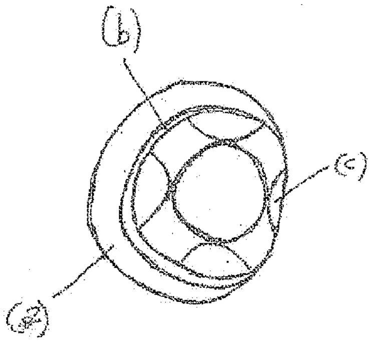
FIGS. 4-13 concerns the main basic features of a circular shape taken as an example.
Figure 5:
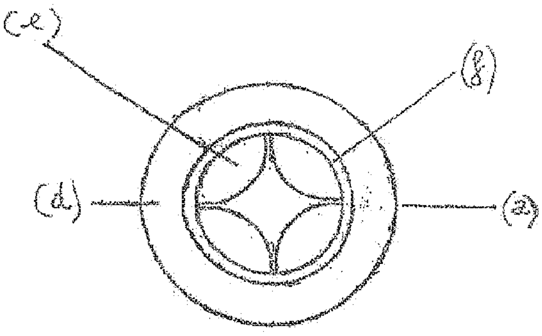
Figure 6:
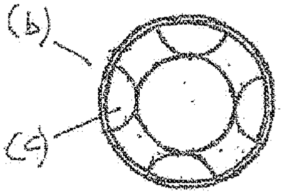
Figure 7:
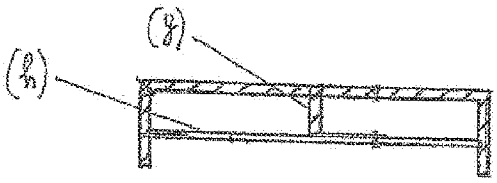
Figure 8:
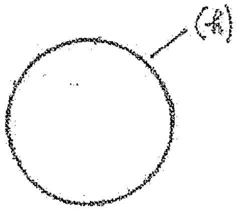

The test has been run using the apparatus schematically shown in FIG. 3.

A microorganisms' aerosol was introduced, at 7 l/min gas flow, into a drying chamber (b) by a nebulizer (c), using compressed air filtered through filter (a). The aerosol is mixed with compressed air, separately delivered through filter (d) to the drying chamber, in order to obtain a 28 l/min flow.

The droplets of contaminated aerosol, which enter the drying chamber, rapidly evaporate.

The droplets are retained into the drying chamber due to their weight, as well as in the evaporation tube (e) when they knock against the tube walls at the angles.

Consequently, only the monodispersed bacteria can reach the filtering material (f) under evaluation.

The gas flows, before and after the material under evaluation, were collected into glass sampling vessels for liquids, at 28 l/min flow, by a vacuum pump. The sampling vessels, before (g) and after (h) the material, work separately and one after the other. The flow through them is selected by a vacuum valve (i).

During the test, the sampling took place for 5 seconds, then the sampling vessel was isolated and the vacuum was created in the other sampling vessel.

In any experiment the formation of the contaminated aerosol lasted 5 minutes. The compressed air of the nebulizer was then closed by the relevant valve and the filtered air flew 2 minutes through the sampling vessels by the vacuum pump.

A sample of the liquid coming from (g) was then diluted, in sequence, 10 times, transferred into "agar plates" and then incubated.

The whole content of the sampling vessel (h) was filtered through a 0.45 micron, cellulose nitrate, analytical membrane. The membrane was then put on an agar layer and incubated.

The incubation was carried out 14 days at 35.degree. C. and, at the end, the number of colonies was counted.

On the basis of ten measurements, the removal efficiency turned out to be >99,999%.

Test 2

Monodispersed Challenge of MS-2

The test has been carried out using an aerosol of monodispersed bacteriophage MS-2.

MS-2 is a polyhedric virus with approximate dimension 0.02 microns which, being non pathogenic to humans, serves to simulate viruses, with similar shape and dimensions, that are pathogenic to humans.

The method is basically identical to TEST 1 and the test was carried out with a 10 l/min flow and with 24 hours incubation at 30.degree. C.

The efficiency turned out to be superior to 99,999%.

On the basis of the results of TEST 2, the filtering system can be considered effective against any microorganism with dimension larger than MS-2 bacteriophage, in particular against Hepatitis C Virus (HCV), Hepatitis B Virus (HBV), Human Immunodeficiency Viruses (HIV), Sp. *Pseudomonas, Staphylococcus aureus, Serratia Marcescescens, Bacillus Anthracis.*

It is worth mentioning that the tests were carried out with monodispersed particles, that represents the most critical situation. In normal conditions, the majority of microorganisms are not monodispersed but, on the contrary, they are in a wide variety of drop forms and of single microorganisms so that the efficiency, in normal condition of use, may be even superior to the tests' results.

The mask, in addition to the inherent barrier due to the filtering material properties, has been drawn to ensure a perfect and safe seal in any situation and to offer improved comfort to the wearer.

In particular, the mask can be equipped with a valve to facilitate the breathing which opens, in response to increased pressure, when the wearer exhales and which allows warm, moist and high —$CO_2$— content air to be rapidly evacuated from the mask interior. The mask is, at the same time, able to close during inhaling and has been projected in an innovative and specific design, in comparison with the prior art, in order to ensure a perfect seal during this phase preventing the microorganisms from passing inside the mask.

For this reason, the valve represents a particular object of the present invention.

The valve shows the main basic features of the similar exhalation systems and the shape, the size and the materials can be chosen out of the commonly known ones.

The main basic features are described with reference to FIGS. 4-9, that concern a circular shape taken as an example.

In particular, the valve (FIG. 4) comprises a valve seat (a) over which is secured a raised valve cover (b), carrying apertures (c).

The seat (FIG. 5) is composed by a flat surface (d), having four elliptical orifices (e) which allow the air flow.

In the centre of the seat (a), a circular, low thickness, relief (f) rises.

The cover (FIGS. 6 and 7) is circular with four apertures (c) (FIG. 4), having semicircle shape, allowing the air passing through. A circular valve flap (h) is attached by an appropriate support (g) to the centre of the internal side of the cover. The flap is made from flexible material and represents the mobile component which opens and closes the valve.

The valve can be made from the various materials suitable for thermoforming, preferably is made from molded polypropylene. The flap is made from an elastic flexible material such as, for example, synthetic rubber.

Figure 9:
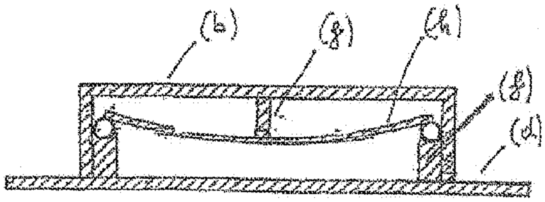

The reciprocal positions of the valve cover, the valve seat and the other components, is shown in FIG. 9.

The valve is attached to the center of the panel 1 of the mask where a circular aperture is also created.

The valve is attached by simply laying the panel 1 on the valve seat (a), taking care of fitting together the opening in the material with the central orifice of the valve seat (a). Then the valve cover (b) is fixed over the valve seat by pressure.

This way, the material of panel 1 is locked between the valve cover and the valve seat.

When the wearer inhales, the valve flap seals against the relief (f), preventing air from flowing, while, when the wearer exhales, the valve flap lift away from the relief (f), letting air pass through.

Consequently, inhaled air enters the mask exclusively through the filter media of the mask whereas exhaled air passes through the aperture of the mask and the orifices in the valve.

Although the working principle of the valve is known, the valve of the present invention provides an additional feature which ensures the highest seal during inhaling in order to avoid any possible contamination by microorganisms.

Figure 10:
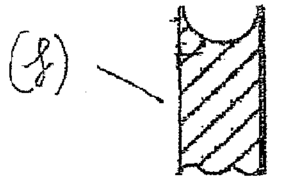
Figure 11:
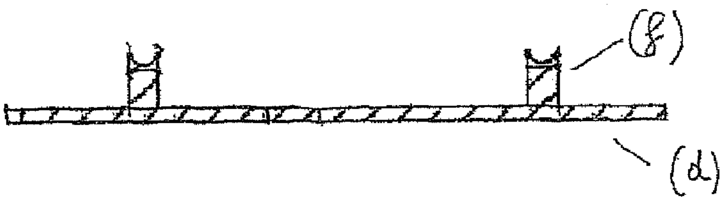
Figure 12:
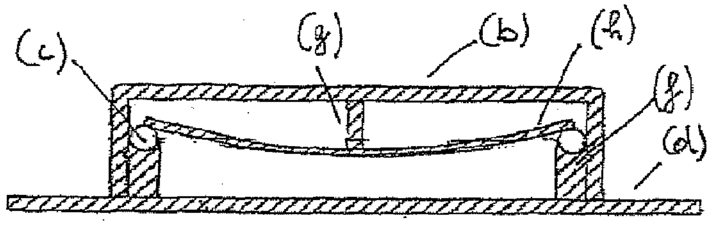

In particular, the relief (f) of the valve seat owns a concave surface (FIGS. 10 and 11) wherein a continues, cylinder shaped, plastic, like an O-ring, lays all along the circumference. The O-ring can be made from synthetic polymers obtained from different monomers and can be produced with different mixtures, for example, with fluoro, silicone or nitrile based mixtures. The ring is designed, in terms of dimensions and structure, to provide the highest seal during closing. In fact, when the valve flap seals against the relief (f), it goes into direct contact with the ring (i) (FIG. 12). Then, due to the dimensions of the flap support (g) and the ring thickness, the valve flap flexes up on the edges.

The flap material, thanks to its intrinsic memory and to the elastic properties, perfectly seals onto the O-ring surface. In addition, the compatibility of the two materials, having the same chemical-physical superficial properties, ensures a perfect adherence.

Consequently the seal efficiency turns out to be dramatically superior to the one obtained by the known masks wherein the valve flap lays flat directly onto the molded material of the valve.

Figure 13:
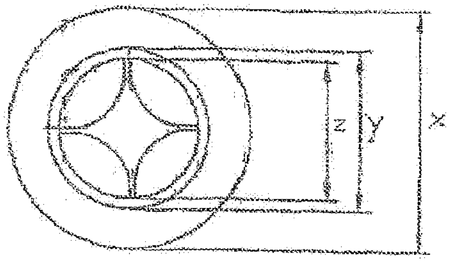
Figure 13:
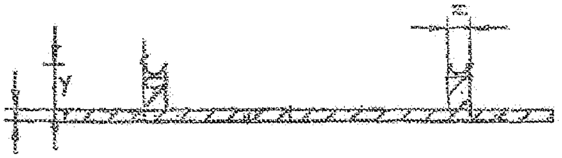
Figure 13:
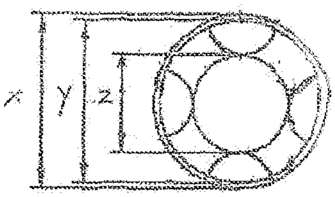
Figure 13:
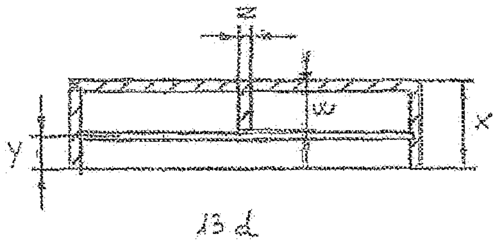
Figure 13:
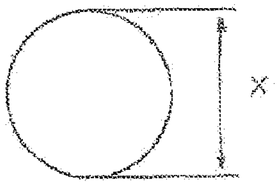

For a better understanding of the valve's structure, some typical dimensions of the different components are listed with reference to FIG. 13.

13*a*: valve seat, front view x: 45 mm y: 30 mm z: 26 mm

13*b*: valve seat, side view x: 1 mm y: 4.2 mm z: 4 mm

13*c*: valve cover, front view x: 32 mm y: 30 mm z: 18 mm

13*d*. valve cover, side view x: 8 mm y: 3 mm z: 1 mm w: 3.5 mm

13*e*: valve flap x (diameter): 30 mm

Due to its inventive features, the valve represents a particular embodiment of the present invention.

To this scope, the above description does not imply any restriction beyond the distinctive feature.

Therefore, the valve can have other shapes, for example a rectangular one, and can be made from other materials. The valve can also be secured to the mask by other conventional and known methods, for example, by polyolefins or EVA based hot melt adhesives.

The mask is also equipped with conventional systems to enable the mask to be closely fitted to wearer's face and to enable its edges to be in tight contact with the different parts of the face.

In particular, the clip 5 improves the fit over the wearer's nose whereas the bands 4 are used to position the mask snugly over the user's head. The bands are made from conventional materials, in particular from a combination of an elastic constituent, such as synthetic rubber, and a thermoplastic constituent, for example polypropylene, chosen for its affinity with the preferred mask's constituent.

Figure 2:
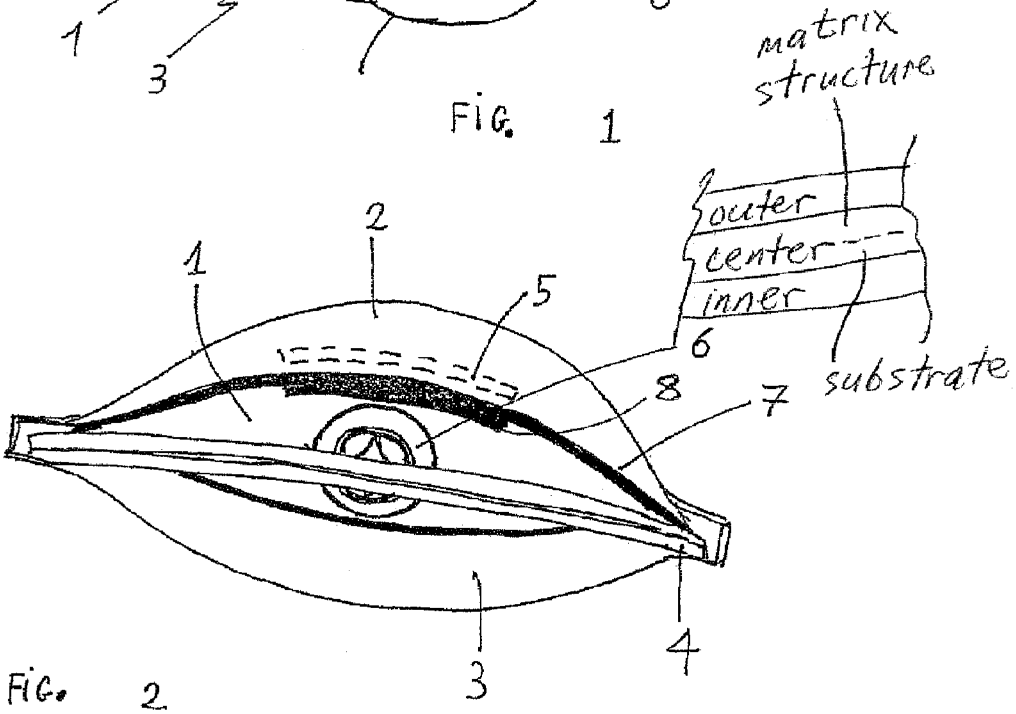
FIG. 2 shows the inside of the mask.

In addition, the mask is equipped, on the edges, with a boundary sealing layer applied all along the perimeter on panel 2 and 3 of FIG. 2. This layer is indicated as 7 in FIG. 2 and is drawn around the mask periphery, on superior and inferior edges of the mask, starting from the side joins. In addition, adjoining this layer, a strip made from the same material (8 in FIG. 2), and some 9 cm long, is applied in the nose clip area. The strip makes the mask more comfortable to wear and, further on, improves the seal between the mask and the face at the nose portion wherein deformations and plies may normally be present.

The sealing layer is made either from a natural rubber latex resin or a silicone based resin or any other suitable material.

As an example, the natural rubber latex is applied in some 2 mm thickness and in unit area typically ranging between 200 and 400 g/m$^2$.

These dimensions and weights are given by way of example only and do not imply any limitation.

The seal layer tightly fits over the wearer's face perfectly adapting to any face shape. The seal layer ensures a leak free contact to the wearer's face, without pin holes and distortions which would allow contaminants to pass through the mask body without being removed by the filtering material.

Furthermore, the material of the boundary sealing layer is very soft and makes the mask more comfortable to wear.

The seal of the mask has been evaluated by a mask proof apparatus obtaining outstanding results.

Test 3

The test was carried out using a bacteria challenge and simulating a real respiration by a Sheffied head and an automatic respirator.

The mask was put on the Sheffied head to simulate the use of a wearer and the head was placed inside the test chamber.

A measured amount of the microorganism *Brevundimonas diminuta* (ATCC19146) was introduced in an aerosol generator and was nebulized within the test chamber.

The artificial lung was switched on and set at 25 breathes/min in order to simulate a normal human respiration. Then the inhaled air was collected in a gurgling vessel filled with 50 ml of salt solution.

After 30 minutes, the microorganisms in solution were counted. The number (Na) of UFC/50 ml of microorganisms which passed through the mask was compared with the number (Nv) of UFC/50 ml of microorganisms determined by a test carried out without the mask.

The result is given in terms of Reduction titre of the microorganism used in the test, by the following formula: R(reduction titre)=(Nv−Na).times.100/Nv=99.99%.

The different components of the mask can be assembled using known technologies such as, for example, heat or ultrasonic welding, adhesive bonding, mechanical clamping. When adhesives are used, they are preferably hot melt adhesives.

The mask of the present invention, thanks to the filtering efficiency of the central layer combined with the outstanding tight seal of the valve and of the boundary sealing layer, owns barrier properties against biological agents never reached by the known similar protection means.

Although particular embodiments of the present invention have been described in the foregoing description, it will be understood by those skilled in the art that any simple modification and rearrangement will not depart from the spirit or essential attributes of the invention which are defined in the following claims.

The invention claimed is:

1. A mask for the protection against biological agents, comprising:

a cup-shaped chamber defined by a central panel, an upper panel, and a lower panel joined together;

each of the central panel, the upper panel, and the lower panel comprised of a plurality of layers, at least one of the layers composed of a cellulose-based substrate supporting a fiber-based matrix structure of borosilicate micro-glass fibers bound together by a vinyl acetate resin, and iii) a silicone based coating imparting hydrophobic properties on the structure and the substrate;

a boundary sealing layer located on perimeter edges of the cup-chamber; and a cylinder-shaped valve located on the outside of the central panel configured to facilitate passage of exhaled air from an interior of the mask to ambient air, the valve comprising a valve seat secured by a raised valve cover, the valve cover including apertures, an upper end of the valve seat including a relief with a concave surface and defining a circumference of the relief, a continuous, cylindrical cross-sectional shaped, O-ring located along an entirety of the concave surface of circumference of the relief, a circular valve flap with outside edges located on a upper side of the O-ring, the valve cover extending over and covering the valve flap, the relief, and the O-ring, the valve cover further including a flap support pressing down on a center of the valve flap.

2. A mask as claimed in claim 1, wherein the plurality of layers comprises three layers and the at least one layer is a central layer of the three layer located intermediate i) an outer layer having a covering function and ii) an inner layer having a shape-retaining function.

3. A mask as claimed in claim 2, wherein the central layer has thickness ranging between 150 and 400 microns and in a amount of between 25 and 65 g/m$^2$.

4. A mask as claimed in claim 2, wherein the inner layer is made from non-woven fabric of one of polypropylene fibers and polyester fibers.

5. A mask as claimed in claim 2, wherein the inner layer is made from non-woven fabric consisting of polypropylene fibers.

6. A mask as claimed in claim 2, wherein the outer layer is made from non-woven fabric of polyolefins, polyester or nylon fibers.

7. A mask as claimed in claim 2, wherein the outer layer is made from meltblown polypropylene fibers.

8. A mask as claimed in claim 1, wherein the boundary sealing layer is a natural rubber latex resin or a silicone based resin.

9. A mask as claimed in claim 1, wherein the boundary sealing layer is made from natural rubber latex applied in a 2 mm thickness and in an amount ranging between 200 and 400 g/m$^2$.

10. A mask as claimed in claim 1, further comprising a nose clip located in the upper panel.

* * * * *